United States Patent
Cowan et al.

(10) Patent No.: US 10,286,152 B2
(45) Date of Patent: *May 14, 2019

(54) QUICK RELEASE PLUNGER

(71) Applicant: BAYER HEALTHCARE LLC, Whippany, NJ (US)

(72) Inventors: Kevin P. Cowan, Allison Park, PA (US); Edward J. Rhinehart, Monroeville, PA (US); Mark Trocki, Cheswick, PA (US); Barry L. Tucker, Verona, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/687,641

(22) Filed: Aug. 28, 2017

(65) Prior Publication Data
US 2018/0008780 A1    Jan. 11, 2018

Related U.S. Application Data

(63) Continuation of application No. 14/930,115, filed on Nov. 2, 2015, now Pat. No. 9,744,305, which is a (Continued)

(51) Int. Cl.
*A61M 5/315*    (2006.01)
*A61M 5/50*    (2006.01)

(52) U.S. Cl.
CPC ........ *A61M 5/31513* (2013.01); *A61M 5/315* (2013.01); *A61M 5/31511* (2013.01); (Continued)

(58) Field of Classification Search
CPC .............. A61M 5/315; A61M 5/31511; A61M 5/31515; A61M 5/31513; A61M 5/5066; A61M 2005/31521
(Continued)

(56) References Cited

U.S. PATENT DOCUMENTS 1,265,537 A    5/1918    Ivan
1,687,323 A    10/1928    Cook
(Continued)

FOREIGN PATENT DOCUMENTS

AU    317487    1/2008
DE    2919978 A1    11/1980
(Continued)

OTHER PUBLICATIONS

"International Preliminary Report on Patentability from Corresponding PCT Application No. PCT/US2015/021171", dated Sep. 20, 2016.
(Continued)

*Primary Examiner* — Manuel A Mendez
(74) *Attorney, Agent, or Firm* — Joseph L. Kent; David Schramm; James R. Stevenson (57) ABSTRACT

A syringe system and components thereof are disclosed. The system may include a syringe body having a hollow lumen, a proximal open end, and a distal end. The syringe body may be configured to house a fluid therein. The syringe system may further include a plunger positioned in the hollow lumen of the syringe body, forming a seal with an inner wall of the syringe body. The plunger may include a removable piston having a shaft extending from the distal end towards the proximal open end, a stopper removably connected to a distal portion of the shaft, and at least one coupler attached to the distal portion of the shaft. The stopper may be configured to slidably move within the hollow lumen to facilitate movement of the fluid within the syringe body. The coupler may be configured to facilitate removal and attachment of the stopper from the piston.

19 Claims, 7 Drawing Sheets

Related U.S. Application Data continuation of application No. 13/792,155, filed on Mar. 10, 2013, now Pat. No. 9,174,003.

(60) Provisional application No. 61/707,690, filed on Sep. 28, 2012.

(52) U.S. Cl.
CPC ...... *A61M 5/31515* (2013.01); *A61M 5/5066* (2013.01); *A61M 2005/31521* (2013.01)

(58) Field of Classification Search
USPC ........ 604/110, 218, 228, 187, 233, 229, 225
See application file for complete search history.

(56) References Cited

U.S. PATENT DOCUMENTS

| | | |
|---|---|---|
| 1,988,480 A | 1/1935 | Campkin |
| 2,392,196 A | 1/1946 | Smith |
| 2,419,401 A | 4/1947 | Hinds |
| 2,702,547 A | 2/1955 | Glass |
| 2,842,126 A | 7/1958 | Brown |
| 3,051,173 A | 8/1962 | Johnson et al. |
| D203,730 S | 2/1966 | Porat |
| 3,270,483 A | 9/1966 | Smoyer et al. |
| 3,348,545 A | 10/1967 | Sarnoff et al. |
| 3,468,471 A | 9/1969 | Linder |
| 3,604,417 A | 9/1971 | Stolzenberg et al. |
| 3,623,474 A | 11/1971 | Heilman |
| 3,645,262 A | 2/1972 | Harrigan |
| 3,701,345 A | 10/1972 | Heilman |
| 3,705,582 A | 12/1972 | Stumpf et al. |
| 3,720,211 A | 3/1973 | Kyrias |
| 3,738,539 A | 6/1973 | Beich |
| 3,752,145 A | 8/1973 | Runnells et al. |
| 3,796,218 A | 3/1974 | Burke et al. |
| 3,809,082 A | 5/1974 | Hurschman |
| 3,812,843 A | 5/1974 | Wootten et al. |
| 3,902,491 A | 9/1975 | Lajus |
| 3,964,139 A | 6/1976 | Kleinmann et al. |
| 3,987,940 A | 10/1976 | Tischlinger |
| 3,998,224 A | 12/1976 | Chiquiar-Arias |
| 4,006,736 A | 2/1977 | Kranys et al. |
| 4,030,498 A | 6/1977 | Tompkins |
| 4,080,967 A | 3/1978 | O'Leary |
| 4,148,316 A | 4/1979 | Xanthopoulos |
| 4,155,490 A | 5/1979 | Glenn |
| 4,159,713 A | 7/1979 | Prais |
| 4,180,006 A | 12/1979 | Ross |
| 4,180,069 A | 12/1979 | Walters |
| 4,226,236 A | 10/1980 | Genese |
| 4,252,118 A | 2/1981 | Richard et al. |
| 4,278,086 A | 7/1981 | Hodgins et al. |
| 4,303,070 A | 12/1981 | Ichikawa et al. |
| 4,345,595 A | 8/1982 | Whitney et al. |
| 4,351,332 A | 9/1982 | Whitney et al. |
| 4,356,822 A | 11/1982 | Winstead-Hall |
| 4,424,720 A | 1/1984 | Bucchianeri |
| 4,452,251 A | 6/1984 | Heilman |
| 4,453,934 A | 6/1984 | Gahwiler et al. |
| 4,464,265 A | 8/1984 | Joyner |
| 4,465,472 A | 8/1984 | Urbaniak |
| 4,465,473 A | 8/1984 | Ruegg |
| 4,475,666 A | 10/1984 | Bilbrey et al. |
| 4,476,381 A | 10/1984 | Rubin |
| 4,490,256 A | 12/1984 | Nussbaumer et al. |
| 4,493,646 A | 1/1985 | Lacour et al. |
| 4,500,310 A | 2/1985 | Christinger |
| 4,529,401 A | 7/1985 | Leslie et al. |
| 4,562,844 A | 1/1986 | Carpenter et al. |
| 4,568,335 A | 2/1986 | Updike et al. |
| 4,573,978 A | 3/1986 | Reilly |
| 4,585,439 A | 4/1986 | Michel |
| 4,604,847 A | 8/1986 | Moulding, Jr. et al. |
| 4,612,010 A | 9/1986 | Hamacher et al. |
| 4,617,016 A | 10/1986 | Blomberg |
| 4,628,969 A | 12/1986 | Jurgens, Jr. et al. |
| 4,636,198 A | 1/1987 | Stade |
| 4,648,872 A | 3/1987 | Kamen |
| 4,650,475 A | 3/1987 | Smith et al. |
| 4,652,260 A | 3/1987 | Fenton, Jr. et al. |
| 4,664,128 A | 5/1987 | Lee |
| 4,676,776 A | 6/1987 | Howson |
| 4,677,980 A | 7/1987 | Reilly et al. |
| 4,677,981 A | 7/1987 | Coursant |
| 4,681,566 A | 7/1987 | Fenton, Jr. et al. |
| 4,685,903 A | 8/1987 | Cable et al. |
| 4,695,271 A | 9/1987 | Goethel |
| 4,705,509 A | 11/1987 | Stade |
| 4,718,463 A | 1/1988 | Jurgens, Jr. et al. |
| 4,722,734 A | 2/1988 | Kolln |
| 4,741,732 A | 5/1988 | Crankshaw et al. |
| 4,741,736 A | 5/1988 | Brown |
| 4,749,109 A | 6/1988 | Kamen |
| 4,755,172 A | 7/1988 | Baldwin |
| 4,767,406 A | 8/1988 | Wadham et al. |
| 4,773,900 A | 9/1988 | Cochran |
| 4,838,857 A | 6/1989 | Strowe et al. |
| 4,840,616 A | 6/1989 | Banks |
| 4,842,581 A | 6/1989 | Davis |
| RE32,974 E | 7/1989 | Porat et al. |
| 4,852,768 A | 8/1989 | Bartsch |
| 4,853,521 A | 8/1989 | Claeys et al. |
| 4,854,324 A | 8/1989 | Hirschman et al. |
| 4,863,427 A | 9/1989 | Cocchi |
| 4,869,720 A | 9/1989 | Chernack |
| 4,878,896 A | 11/1989 | Garrison et al. |
| 4,908,022 A | 3/1990 | Haber |
| 4,911,695 A | 3/1990 | Lindner |
| 4,923,443 A | 5/1990 | Greenwood et al. |
| 4,929,238 A | 5/1990 | Baum |
| 4,931,043 A | 6/1990 | Ray et al. |
| 4,932,941 A | 6/1990 | Min et al. |
| 4,936,833 A | 6/1990 | Sams |
| 4,943,279 A | 7/1990 | Samiotes et al. |
| 4,946,009 A | 8/1990 | Knutson |
| 4,950,243 A | 8/1990 | Estruch |
| 4,966,601 A | 10/1990 | Draenert |
| 4,969,874 A | 11/1990 | Michel et al. |
| 4,973,309 A | 11/1990 | Sultan |
| 4,978,335 A | 12/1990 | Arthur, III |
| 4,988,337 A | 1/1991 | Ito |
| 4,997,423 A | 3/1991 | Okuda et al. |
| 5,000,735 A | 3/1991 | Whelan |
| 5,007,904 A | 4/1991 | Densmore et al. |
| 5,019,045 A | 5/1991 | Lee |
| 5,024,663 A | 6/1991 | Yum, II |
| 5,033,650 A | 7/1991 | Colin et al. |
| 5,034,004 A | 7/1991 | Crankshaw |
| 5,047,014 A | 9/1991 | Mosebach et al. |
| 5,059,179 A | 10/1991 | Quatrochi et al. |
| 5,062,832 A | 11/1991 | Seghi |
| 5,078,683 A | 1/1992 | Sancoff et al. |
| 5,084,017 A | 1/1992 | Maffetone |
| 5,085,638 A | 2/1992 | Farbstein et al. |
| 5,085,643 A | 2/1992 | Larkin et al. |
| 5,090,962 A | 2/1992 | Landry, Jr. et al. |
| 5,093,079 A | 3/1992 | Bakaitis et al. |
| 5,094,148 A | 3/1992 | Haber et al. |
| 5,104,374 A | 4/1992 | Bishko et al. |
| 5,106,372 A | 4/1992 | Ranford |
| 5,106,379 A | 4/1992 | Leap |
| 5,122,118 A | 6/1992 | Haber et al. |
| 5,135,507 A | 8/1992 | Haber et al. |
| 5,147,311 A | 9/1992 | Pickhard |
| 5,153,827 A | 10/1992 | Coutre et al. |
| 5,176,642 A | 1/1993 | Clement |
| 5,181,912 A | 1/1993 | Hammett |
| 5,226,897 A | 7/1993 | Nevens et al. |
| 5,236,416 A | 8/1993 | McDaniel et al. |
| 5,242,408 A | 9/1993 | Jhuboo et al. |
| 5,246,423 A | 9/1993 | Farkas |
| 5,254,086 A | 10/1993 | Palmer et al. |
| 5,254,101 A | 10/1993 | Trombley, III |

(56) References Cited

U.S. PATENT DOCUMENTS

| | | |
|---|---|---|
| 5,256,154 A | 10/1993 | Liebert et al. |
| 5,256,157 A | 10/1993 | Samiotes et al. |
| 5,269,762 A | 12/1993 | Armbruster et al. |
| 5,275,582 A | 1/1994 | Wimmer |
| 5,279,569 A | 1/1994 | Neer et al. |
| 5,282,792 A | 2/1994 | Imbert |
| 5,282,858 A | 2/1994 | Bisch et al. |
| 5,300,031 A | 4/1994 | Neer et al. |
| 5,308,330 A | 5/1994 | Grimard |
| 5,314,415 A | 5/1994 | Liebert et al. |
| 5,317,506 A | 5/1994 | Coutre et al. |
| 5,324,273 A | 6/1994 | Discko, Jr. |
| 5,336,189 A | 8/1994 | Sealfon |
| 5,338,309 A | 8/1994 | Imbert |
| 5,342,298 A | 8/1994 | Michaels et al. |
| 5,353,691 A | 10/1994 | Haber et al. |
| 5,354,287 A | 10/1994 | Wacks |
| 5,356,375 A | 10/1994 | Higley |
| 5,356,393 A | 10/1994 | Haber et al. |
| 5,373,684 A | 12/1994 | Vacca |
| 5,380,285 A | 1/1995 | Jenson |
| 5,383,858 A | 1/1995 | Reilly et al. |
| 5,389,075 A | 2/1995 | Vladimirsky |
| 5,397,313 A | 3/1995 | Gross |
| 5,411,488 A | 5/1995 | Pagay et al. |
| 5,413,563 A | 5/1995 | Basile et al. |
| 5,425,716 A | 6/1995 | Kawasaki et al. |
| 5,429,602 A | 7/1995 | Hauser |
| 5,429,611 A | 7/1995 | Rait |
| 5,431,627 A | 7/1995 | Pastrone et al. |
| 5,433,712 A | 7/1995 | Stiles et al. |
| 5,439,452 A | 8/1995 | McCarty |
| 5,445,622 A | 8/1995 | Brown |
| 5,451,211 A | 9/1995 | Neer et al. |
| 5,456,670 A | 10/1995 | Neer et al. |
| 5,478,314 A | 12/1995 | Malenchek |
| 5,484,413 A | 1/1996 | Gevorgian |
| 5,512,054 A | 4/1996 | Morningstar |
| 5,520,653 A | 5/1996 | Reilly et al. |
| 5,531,698 A | 7/1996 | Olsen |
| 5,531,710 A | 7/1996 | Dang et al. |
| 5,533,981 A | 7/1996 | Mandro et al. |
| 5,535,746 A | 7/1996 | Hoover et al. |
| 5,540,660 A | 7/1996 | Jenson |
| 5,545,140 A | 8/1996 | Conero et al. |
| 5,573,515 A | 11/1996 | Wilson et al. |
| 5,593,386 A | 1/1997 | Helldin |
| 5,624,408 A | 4/1997 | Helldin |
| 5,658,261 A | 8/1997 | Neer et al. |
| 5,662,612 A | 9/1997 | Niehoff |
| 5,681,285 A | 10/1997 | Ford et al. |
| 5,681,286 A | 10/1997 | Niehoff |
| 5,683,367 A | 11/1997 | Jordan et al. |
| 5,688,252 A | 11/1997 | Matsuda et al. |
| 5,695,477 A | 12/1997 | Sfikas |
| 5,722,951 A | 3/1998 | Marano |
| 5,735,825 A | 4/1998 | Stevens et al. |
| 5,738,655 A | 4/1998 | Vallelunga |
| 5,738,659 A | 4/1998 | Neer et al. |
| 5,741,227 A | 4/1998 | Sealfon |
| 5,741,232 A | 4/1998 | Reilly et al. |
| 5,779,675 A | 7/1998 | Reilly et al. |
| 5,782,803 A | 7/1998 | Jentzen |
| 5,785,682 A | 7/1998 | Grabenkort |
| 5,795,333 A | 8/1998 | Reilly et al. |
| 5,807,334 A | 9/1998 | Hodosh et al. |
| 5,808,203 A | 9/1998 | Nolan, Jr. et al. |
| 5,827,219 A | 10/1998 | Uber, III et al. |
| 5,827,262 A | 10/1998 | Neftel et al. |
| 5,840,026 A | 11/1998 | Uber, III et al. |
| RE35,979 E | 12/1998 | Reilly et al. |
| 5,865,805 A | 2/1999 | Ziemba |
| 5,873,861 A | 2/1999 | Hitchins et al. |
| 5,879,336 A | 3/1999 | Brinon |
| 5,882,343 A | 3/1999 | Wilson et al. |
| 5,899,885 A | 5/1999 | Reilly et al. |
| 5,902,276 A | 5/1999 | Namey, Jr. |
| 5,913,844 A | 6/1999 | Ziemba et al. |
| 5,919,167 A | 7/1999 | Mulhauser et al. |
| 5,938,637 A | 8/1999 | Austin et al. |
| 5,938,639 A | 8/1999 | Reilly et al. |
| 5,944,694 A | 8/1999 | Hitchins et al. |
| 5,947,929 A | 9/1999 | Trull |
| 5,947,935 A | 9/1999 | Rhinehart et al. |
| 5,954,697 A | 9/1999 | Srisathapat et al. |
| 5,954,700 A | 9/1999 | Kovelman |
| 5,997,502 A | 12/1999 | Reilly et al. |
| 5,997,511 A | 12/1999 | Curie et al. |
| 6,004,300 A | 12/1999 | Butcher et al. |
| 6,017,330 A | 1/2000 | Hitchins et al. |
| 6,042,565 A | 3/2000 | Hirschman et al. |
| 6,048,334 A | 4/2000 | Hirschman et al. |
| 6,059,756 A | 5/2000 | Yeh |
| 6,080,136 A | 6/2000 | Trull et al. |
| 6,083,197 A | 7/2000 | Umbaugh |
| 6,083,200 A | 7/2000 | Grimm et al. |
| 6,090,064 A | 7/2000 | Reilly et al. |
| 6,099,502 A | 8/2000 | Duchon et al. |
| 6,129,712 A | 10/2000 | Sudo et al. |
| 6,162,200 A | 12/2000 | Sawa et al. |
| 6,196,999 B1 | 3/2001 | Goethel et al. |
| 6,221,045 B1 | 4/2001 | Duchon et al. |
| 6,224,577 B1 | 5/2001 | Dedola et al. |
| 6,267,749 B1 | 7/2001 | Miklos et al. |
| 6,312,410 B1 | 11/2001 | Yamamoto |
| 6,315,758 B1 | 11/2001 | Neer et al. |
| 6,322,535 B1 | 11/2001 | Hitchins et al. |
| RE37,487 E | 12/2001 | Reilly et al. |
| 6,336,913 B1 | 1/2002 | Spohn et al. |
| 6,339,718 B1 | 1/2002 | Zatezalo et al. |
| 6,345,262 B1 | 2/2002 | Madden |
| 6,368,307 B1 | 4/2002 | Ziemba et al. |
| 6,432,089 B1 | 8/2002 | Kakimi et al. |
| 6,447,487 B1 | 9/2002 | Cane' |
| 6,511,459 B1 | 1/2003 | Fago |
| 6,517,516 B1 | 2/2003 | Caizza |
| 6,533,758 B1 | 3/2003 | Staats et al. |
| 6,569,127 B1 | 5/2003 | Fago et al. |
| 6,582,399 B1 | 6/2003 | Smith et al. |
| 6,585,700 B1 | 7/2003 | Trocki et al. |
| 6,652,489 B2 | 11/2003 | Trocki et al. |
| 6,659,979 B2 | 12/2003 | Neer et al. |
| 6,669,663 B1 | 12/2003 | Thompson |
| 6,676,635 B2 | 1/2004 | Nemoto |
| 6,733,477 B2 | 5/2004 | Cowan et al. |
| 6,733,478 B2 | 5/2004 | Reilly et al. |
| 6,752,789 B2 | 6/2004 | Duchon et al. |
| 6,764,466 B1 | 7/2004 | Staats et al. |
| 6,808,513 B2 | 10/2004 | Reilly et al. |
| 6,817,990 B2 | 11/2004 | Yap et al. |
| 6,958,053 B1 | 10/2005 | Reilly |
| 7,018,363 B2 | 3/2006 | Cowan et al. |
| 7,025,757 B2 | 4/2006 | Reilly et al. |
| 7,029,459 B2 | 4/2006 | Reilly |
| 7,240,882 B2 | 7/2007 | Degentesh et al. |
| 7,264,612 B2 | 9/2007 | Nemoto |
| 7,300,417 B1 | 11/2007 | Goethel et al. |
| 7,337,538 B2 | 3/2008 | Moutafis et al. |
| 7,344,520 B2 | 3/2008 | Nemoto |
| 7,393,341 B2 | 7/2008 | Nemoto |
| 7,399,293 B2 | 7/2008 | Oyibo et al. |
| 7,419,478 B1 | 9/2008 | Reilly et al. |
| 7,455,659 B2 | 11/2008 | Nemoto et al. |
| 7,462,166 B2 | 12/2008 | Kowan et al. |
| 7,465,290 B2 | 12/2008 | Reilly |
| 7,497,843 B1 | 3/2009 | Castillo et al. |
| 7,501,092 B2 | 3/2009 | Chen |
| 7,503,906 B2 | 3/2009 | Nemoto |
| 7,540,856 B2 | 6/2009 | Hitchins |
| 7,553,294 B2 | 6/2009 | Lazzaro et al. |
| 7,566,326 B2 | 7/2009 | Duchon et al. |
| 7,666,169 B2 | 2/2010 | Cowan et al. |
| 7,682,345 B2 | 3/2010 | Savage |
| 7,695,457 B2 | 4/2010 | Nemoto |

(56) References Cited

U.S. PATENT DOCUMENTS

| | | |
|---|---|---|
| 7,803,134 B2 | 9/2010 | Sharifi et al. |
| 7,854,726 B2 | 12/2010 | Fago et al. |
| 7,875,005 B2 | 1/2011 | Nemoto |
| 7,972,306 B2 | 7/2011 | Shearn |
| 7,998,133 B2 | 8/2011 | Fago et al. |
| 8,012,124 B1 | 9/2011 | Fago et al. |
| 8,012,125 B1 | 9/2011 | Fago et al. |
| 8,038,656 B2 | 10/2011 | Lloyd et al. |
| 8,070,732 B2 | 12/2011 | Rochette |
| 8,105,293 B2 | 1/2012 | Pickhard |
| 8,133,203 B2 | 3/2012 | Hack |
| 8,172,814 B2 | 5/2012 | Cane et al. |
| 8,177,757 B2 | 5/2012 | Nemoto et al. |
| 8,262,644 B2 | 9/2012 | Fago et al. |
| 8,308,689 B2 | 11/2012 | Lewis |
| 8,353,879 B2 | 1/2013 | Goethel et al. |
| 8,454,560 B2 | 6/2013 | Strobl |
| 8,475,415 B2 | 7/2013 | Schiller et al. |
| 8,480,631 B2 | 7/2013 | Wotton et al. |
| 8,574,200 B2 | 11/2013 | Hack |
| 8,585,658 B2 | 11/2013 | Forstreuter |
| 8,597,246 B1 | 12/2013 | Fago et al. |
| 8,613,730 B2 | 12/2013 | Hieb et al. |
| 8,628,495 B2 | 1/2014 | Horton et al. |
| 8,721,596 B2 | 5/2014 | Trocki et al. |
| 8,740,854 B2 | 6/2014 | Schiller et al. |
| 8,740,856 B2 | 6/2014 | Quinn et al. |
| 8,845,596 B2 | 9/2014 | Berman et al. |
| 8,851,866 B2 | 10/2014 | Moutafis et al. |
| 8,857,674 B2 | 10/2014 | Nighy et al. |
| 8,864,712 B1 | 10/2014 | Fago et al. |
| 8,926,569 B2 | 1/2015 | Bisegna et al. |
| 8,932,255 B1 | 1/2015 | Fago et al. |
| 9,173,995 B1 | 11/2015 | Tucker et al. |
| 9,174,003 B2 * | 11/2015 | Cowan ............... A61M 5/315 |
| 9,199,033 B1 | 12/2015 | Cowan et al. |
| 9,474,857 B2 | 10/2016 | Riley et al. |
| 9,844,622 B2 | 12/2017 | Savage et al. |
| 2001/0047153 A1 | 11/2001 | Trocki et al. |
| 2002/0022807 A1 | 2/2002 | Duchon et al. |
| 2002/0068905 A1 | 6/2002 | Cowan et al. |
| 2002/0128606 A1 | 9/2002 | Cowan et al. |
| 2002/0165491 A1 | 11/2002 | Reilly |
| 2002/0177811 A1 | 11/2002 | Reilly et al. |
| 2003/0004468 A1 | 1/2003 | Righi et al. |
| 2003/0009133 A1 | 1/2003 | Ramey |
| 2003/0060754 A1 | 3/2003 | Reilly et al. |
| 2003/0120219 A1 | 6/2003 | Nielsen |
| 2003/0153877 A1 | 8/2003 | Huang et al. |
| 2003/0163089 A1 | 8/2003 | Bynum |
| 2003/0216683 A1 | 11/2003 | Shekalim |
| 2003/0236800 A1 | 12/2003 | Goeltzenleuchter et al. |
| 2004/0006314 A1 | 1/2004 | Campbell et al. |
| 2004/0039368 A1 | 2/2004 | Reilly et al. |
| 2004/0064041 A1 | 4/2004 | Lazzaro et al. |
| 2004/0068223 A1 | 4/2004 | Reilly |
| 2004/0074453 A1 | 4/2004 | Roelle et al. |
| 2004/0116861 A1 | 6/2004 | Trocki et al. |
| 2004/0133153 A1 | 7/2004 | Trocki et al. |
| 2004/0133161 A1 | 7/2004 | Trocki et al. |
| 2004/0133162 A1 | 7/2004 | Trocki et al. |
| 2004/0133183 A1 | 7/2004 | Trocki et al. |
| 2004/0158205 A1 | 8/2004 | Savage |
| 2004/0186437 A1 | 9/2004 | Frenette et al. |
| 2004/0243022 A1 | 12/2004 | Carney et al. |
| 2004/0243067 A1 | 12/2004 | Sibbitt |
| 2005/0015056 A1 | 1/2005 | Duchon et al. |
| 2005/0113754 A1 | 5/2005 | Cowan et al. |
| 2005/0240149 A1 | 10/2005 | Lu |
| 2006/0129104 A1 | 6/2006 | Cowan et al. |
| 2006/0173411 A1 | 8/2006 | Barere |
| 2007/0123830 A1 | 5/2007 | Johannes et al. |
| 2007/0191785 A1 | 8/2007 | Barere et al. |
| 2009/0247957 A1 | 10/2009 | Heutschi |
| 2010/0016796 A1 | 1/2010 | Derichs |
| 2010/0057014 A1 | 3/2010 | Cane et al. |
| 2010/0222674 A1 | 9/2010 | Cowan et al. |
| 2010/0318030 A1 | 12/2010 | Jenkins |
| 2011/0034882 A1 | 2/2011 | Quinn et al. |
| 2011/0178500 A1 | 7/2011 | Shang et al. |
| 2011/0224611 A1 | 9/2011 | Lum et al. |
| 2012/0039809 A1 | 2/2012 | Levinson et al. |
| 2012/0184920 A1 | 7/2012 | Okihara et al. |
| 2012/0286187 A1 | 11/2012 | Spolski |
| 2013/0150806 A1 | 6/2013 | Fangrow, Jr. |
| 2013/0211325 A1 | 8/2013 | Wang et al. |
| 2013/0317427 A1 | 11/2013 | Brereton et al. |
| 2013/0317480 A1 | 11/2013 | Reber et al. |
| 2013/0338605 A1 | 12/2013 | Chen |
| 2014/0031763 A1 | 1/2014 | Soma et al. |
| 2014/0094749 A1 | 4/2014 | Cowan et al. |
| 2014/0200483 A1 | 7/2014 | Fojtik |
| 2014/0243746 A1 | 8/2014 | Trocki et al. |
| 2014/0330216 A1 | 11/2014 | Weaver et al. |

FOREIGN PATENT DOCUMENTS

| | | |
|---|---|---|
| DE | 3227417 A1 | 2/1983 |
| DE | 4017920 A1 | 12/1991 |
| DE | 19601214 A1 | 8/1996 |
| DE | 19633530 A1 | 2/1998 |
| EP | 0111724 A2 | 6/1984 |
| EP | 0160303 A2 | 11/1985 |
| EP | 0164904 A2 | 12/1985 |
| EP | 0308380 A2 | 3/1989 |
| EP | 0319275 A1 | 6/1989 |
| EP | 0320168 A1 | 6/1989 |
| EP | 0323321 A1 | 7/1989 |
| EP | 0346950 A2 | 12/1989 |
| EP | 0364010 A2 | 4/1990 |
| EP | 0384657 A1 | 8/1990 |
| EP | 0482677 A1 | 4/1992 |
| EP | 0523343 A1 | 1/1993 |
| EP | 0523434 A1 | 1/1993 |
| EP | 0567944 A1 | 11/1993 |
| EP | 0567945 A1 | 11/1993 |
| EP | 0584531 A2 | 3/1994 |
| EP | 0736306 A1 | 10/1996 |
| EP | 0749757 A2 | 12/1996 |
| EP | 0900573 A2 | 3/1999 |
| EP | 0919251 A2 | 6/1999 |
| EP | 0951306 A2 | 10/1999 |
| EP | 0951306 B1 | 10/1999 |
| EP | 1002551 A2 | 5/2000 |
| EP | 1166807 A1 | 1/2002 |
| EP | 1166807 B1 | 11/2005 |
| GB | 847914 A | 9/1960 |
| GB | 1380873 A | 1/1975 |
| GB | 2108852 A | 5/1983 |
| JP | S61500415 A | 3/1986 |
| JP | S6327770 A | 2/1988 |
| JP | S6368177 A | 3/1988 |
| JP | 2001029466 A | 2/2001 |
| JP | 4462798 B2 | 5/2010 |
| JP | D1398129 | 10/2010 |
| JP | D1398130 | 10/2010 |
| JP | D1400385 | 11/2010 |
| JP | D1400386 | 11/2010 |
| JP | D1400551 | 11/2010 |
| JP | D1400552 | 11/2010 |
| WO | 8002376 A1 | 11/1980 |
| WO | 8500292 A1 | 1/1985 |
| WO | 8502256 A1 | 5/1985 |
| WO | 8906145 A1 | 7/1989 |
| WO | 8909071 A1 | 10/1989 |
| WO | 8911310 A1 | 11/1989 |
| WO | 9001962 A1 | 3/1990 |
| WO | 9104759 A1 | 4/1991 |
| WO | 9221391 A1 | 12/1992 |
| WO | 9413336 A1 | 6/1994 |
| WO | 9425089 A1 | 11/1994 |
| WO | 9632975 A1 | 10/1996 |
| WO | 9707841 A2 | 3/1997 |
| WO | 9736635 A1 | 10/1997 |

(56) References Cited

FOREIGN PATENT DOCUMENTS

| WO | 9820920 | A2 | 5/1998 |
|---|---|---|---|
| WO | 9965548 | A1 | 12/1999 |
| WO | 0137903 | A2 | 5/2001 |
| WO | 0137905 | A2 | 5/2001 |
| WO | 0204049 | A1 | 1/2002 |
| WO | 03101527 | A1 | 12/2003 |
| WO | 2004035289 | A1 | 4/2004 |
| WO | 2005053771 | A2 | 6/2005 |
| WO | 2007130061 | A1 | 11/2007 |
| WO | 2010139793 | A1 | 12/2010 |
| WO | 2011129175 | A1 | 10/2011 |
| WO | 2012124028 | A1 | 9/2012 |
| WO | 2012155035 | A1 | 11/2012 |
| WO | 2015006430 | A1 | 1/2015 |
| WO | 2016069711 | A1 | 5/2016 |
| WO | 2016069714 | A1 | 5/2016 |

OTHER PUBLICATIONS

"International Search Report and Written Opinion from corresponding PCT Application No. PCT/US2015/021171", dated Jun. 23, 2015.
"Supplementary European Search Report in EP App. EP15765821", dated Oct. 24, 2017.
"Extended European Search Report and Opinion from EP15823049", dated Feb. 1, 2017.
"International Search Report and Written Opinion from PCT Application No. PCT/US2016/059245", dated Mar. 10, 2017.
"International Search Report and Written Opinion from PCT Application No. PCT/US2016/059246", dated Dec. 1, 2016.
Brochure for "Angiomat 6000" of Liebel-Farsheim, 2111 E. Galbraith Road, Cincinnati, OH 45215, © 1987.
Brochure for "Angiomat CT" of Liebel-Farsheim, 2111 E. Galbraith Road, Cincinnati, OH 45215, © 1988.
Brochure for "Cordis Lymphography Injector," Cordis Corporation, Miami, FL 33137 (1972).
Brochure for "PercuPump 1A" of E-Z-Em, Inc, 717 Main Street, Westbury, NY 11590, © 1990.
Brochure for the "The First and Only True Injection System," Medrad Mark V System, Control No. 85106-00-BA-02, Nov. 1988.
Non-Final Office Action dated Mar. 28, 2013 in related case U.S. Appl. No. 12/728,869.
Feb. 23, 2015 ISR and WO from PCT/US2014/067435.
FOA dated Mar. 28, 2013 from U.S. Appl. No. 12/728,869.
Injektron 82 MRT User Instructions, Version MR2, CE0535, Mediron GmbH(Mar. 10, 1999).
International Preliminary Report of Patentability dated Jan. 12, 2016 from PCT/US2014/045923.
International Search Report & Written Opinion for International Application No. PCT/US2004/039225, ISA/US, dated May 12, 2006.
International Search Report for Counterpart PCT Application No. PCT/US00/32271 dated Jul. 3, 2001.
International Search Report for International Application No. PCT/AU01/00830, dated Nov. 1, 2001.
International Search Report for International Application No. PCT/US03/17305, dated Oct. 21, 2003.
IPRP dated Jan. 12, 2016 from PCT/US2014/045923.
ISR dated Oct. 30, 2014 from PCT/US2014/045923.
ISR dated May 12, 2006 by PCT/US2004/039225.
ISR from PCT/US97/20122, dated Jun. 30, 1998.
Liebel-Flarsheim company—Angiomat 6000 Digital Injection System Operator's Manual, 600950 Rev 1 (1990); p. 3-6 TO 3-8, 4-52 to 4-56.
Medrad Envision CT Injector Operation Manual, EOM 700E, 92401-T-123 Rev E, Copyright 1995.
Medrad Envision CT Injector Operation Manual, EOM 700E, 92401-T-123 Rev E, pp. 2-10 to 2-11 and pp. 2-30 b 2-35(Copyright 1995).
Medrad, Mark V/Mark V Plus Injector Operation Manual,KMP 805P Rev. B (1990); pp. 1-18 to 1-28, 3-7 to 3-13, 14-1 to 14-4.
Supplementary ESR from EP 01949108 dated Apr. 13, 2007.
Supplementary ESR from EP 01949108 dated Apr. 25, 2007.
Supplementary European Search Report dated Apr. 14, 2016 from EP13842045.
Supplementary Partial European Search Report for EP 01949108 dated Apr. 13, 2007.
Supplementary Partial European Search Report for EP 01949108 dated Apr. 25, 2007.
European Search Report dated Apr. 27, 2015 from corresponding EP Application No. EP14174725.
The International Preliminary Report on Patentability dated Apr. 9, 2015 from corresponding PCT Application No. PCT/US2013/061384.
International Search Report from corresponding PCT Application PCT/US2013/061384 dated Feb. 20, 2014.
U.S. Appl. No. 09/448,835, filed Nov. 24, 1999.
U.S. Appl. No. 09/731,108, filed Dec. 6, 2000.
U.S. Appl. No. 10/159,592, filed May 30, 2002.
U.S. Appl. No. 10/166,848, filed Jun. 10, 2002.
U.S. Appl. No. 10/174,631, filed Jun. 19, 2002.
U.S. Appl. No. 10/174,639 filed Jun. 19, 2002.
U.S. Appl. No. 10/287,167, filed Nov. 4, 2002.
U.S. Appl. No. 10/380,188, filed Mar. 10, 2003.
U.S. Appl. No. 10/606,157, filed Jun. 25, 2003.
U.S. Appl. No. 10/606,157, filed Nov. 25, 2003.
U.S. Appl. No. 10/619,137, filed Jul. 14, 2003.
U.S. Appl. No. 10/668,643, filed Sep. 23, 2003.
U.S. Appl. No. 10/668,673, filed Sep. 23, 2003.
U.S. Appl. No. 10/669,144, filed Sep. 23, 2003.
U.S. Appl. No. 10/669,148, filed Sep. 23, 2003.
U.S. Appl. No. 10/670,154, filed Sep. 23, 2003.
U.S. Appl. No. 10/722,370, filed Nov. 25, 2003.
WO dated Oct. 30, 2014 from PCT/US2014/045923.

* cited by examiner

QUICK RELEASE PLUNGER

CROSS REFERENCE TO RELATED APPLICATIONS

This application is a Continuation of U.S. application Ser. No. 14/930,115, filed Nov. 2, 2015, now U.S. Pat. No. 9,744,305, which is a Continuation of Ser. No. 13/792,155, filed Mar. 10, 2013, now U.S. Pat. No. 9,174,003, and claims the benefit of U.S. Provisional Patent Application No. 61/707,690, filed Sep. 28, 2012, and entitled "QUICK RELEASE PLUNGER" the entire contents of which are hereby incorporated by reference.

BACKGROUND

A number of injector-actuated syringes and powered injectors have been developed for use in medical procedures, such as, for example, angiography, computed tomography, and nuclear magnetic resonance. Numerous advances have been made in the area of injector-actuated syringes and power injectors for use therewith. Nonetheless, newly developed and developing medical procedures constantly test the limits of current injector systems. For example, some procedures require the use of high pressures but also require physiochemical properties of the syringe that make attainment of high pressures difficult. Changes in syringes to meet the requirements of the newly developed and developing medical procedures may result in necessary changes to other portions of the injector to properly operate with the syringe, which puts care providers at the disadvantage of having to obtain new and costly injectors each time a new syringe is developed.

BRIEF SUMMARY

In an embodiment, a syringe system may include a syringe body having a hollow lumen, a proximal open end, and a distal end. The syringe body may be configured to house a fluid therein. The syringe system may further include a plunger positioned in the hollow lumen of the syringe body, forming a seal with an inner wall of the syringe body. The plunger may include a removable piston having a shaft extending from the distal end towards the proximal open end, a stopper removably connected to a distal portion of the shaft, and at least one coupler attached to the distal portion of the shaft. The stopper may be configured to slidably move within the hollow lumen to facilitate movement of the fluid within the syringe body. The coupler may be configured to facilitate removal and attachment of the stopper from the piston.

In an embodiment, a plunger apparatus that can be at least partially removed from a syringe may include a removable piston having a shaft extending from a distal end of the syringe towards a proximal open end of the syringe, a stopper removably connected to a distal portion of the shaft, and at least one coupler attached to the distal portion of the shaft. The stopper may be configured to slidably move within a hollow lumen of the syringe to facilitate movement of fluid within the syringe. The coupler may be configured to facilitate removal and attachment of the stopper from the piston.

In an embodiment, hydraulically-activated plunger in a fluid delivery system may include a first syringe comprising a first diameter, a proximal end, a distal end having an aperture, and hollow lumen configured to house a fluid therein, and a stopper configured to slidably move within the hollow lumen to facilitate movement of the fluid within the hollow lumen, an internal piston having a distal end and a proximal end. The distal end may be removably attached to the stopper and configured to move the stopper within the hollow lumen of the first syringe, and the proximal end may be fluidly attached to a second syringe having a proximally positioned tip and a second diameter that is smaller than the first diameter. The plunger may further include a third syringe having a distally positioned tip and a third diameter that is smaller than the first diameter, wherein the distally positioned tip of the third syringe is in fluid communication with the proximally positioned tip of the second syringe and an external piston fluidly connected to the third syringe. The external piston may include a plunger and the second syringe and the third syringe may each contain an incompressible fluid sealed therein.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

For purposes of the description hereinafter, the terms "upper," "lower," "right," "left," "vertical," "horizontal," "top," "bottom," "lateral," "longitudinal," and derivatives thereof shall relate to the orientation of embodiments disclosed in the figures. However, embodiments may assume alternative variations and step sequences, except where expressly specified to the contrary. The specific devices and processes illustrated in the attached drawings and described in the following specification, are exemplary embodiments. Hence, physical characteristics related to the embodiments disclosed herein are not to be considered as limiting.

The word "proximal" refers to a direction relatively closer to a clinician or operator using the device described herein, and the word "distal" refers to a direction relatively further from the clinician or operator. For example, the end of a syringe placed nearest the body of a patient is considered a distal end of the syringe, while the end closes to the clinician is a proximal end of the syringe. The terms "axial" or "axially" refer generally to an axis around which the particular objects being referred to are preferably formed (although not necessarily symmetrically therearound). The term "radial" refers generally to a direction normal to the axis or along a radius of an object having a circular cross-section.

Various embodiments are directed to plungers for syringes, including stoppers that may be connected and disconnected from the piston. In various embodiments, such plungers may be manually, hydraulically, or electrically activated. In the embodiments disclosed herein, the same injector can be used for a variety of different syringes because of the ease of attaching and removing the piston portion of the syringe to the stopper portion through the use of a coupler. Furthermore, the present disclosure provides a quick and easy solution for care providers because the piston can be inserted and connected to the stopper without a specific orientation. For example, a user may advance the piston forward until it engages with the connector by snapping into place, regardless of orientation, as will be described in greater detail herein. In addition, a simple ¼ turn twist at any orientation may allow for detachment of the two elements.

Figure 1:
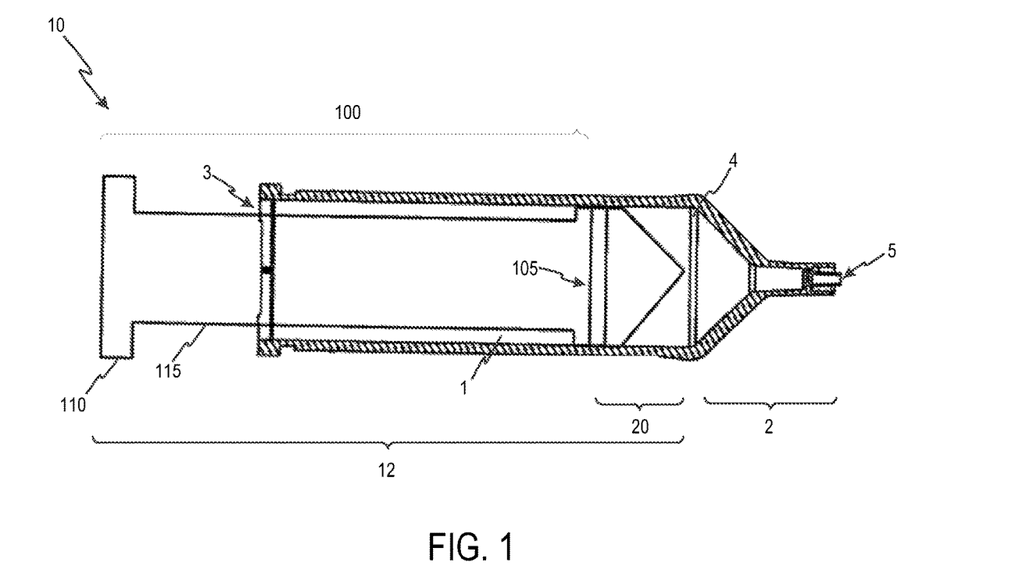
FIG. 1 depicts a side view of a syringe according to an embodiment.

FIG. 1 depicts a syringe, generally designated 10, that may include a cylindrical syringe body 1 defining a hollow lumen 4 therein, an open proximal end 3, and a conical shaped distal end 2 having an aperture 5. A plunger, generally designated 12, may be positioned in the hollow lumen 4 of the syringe body 1 extending from the conical shaped distal end 2 and towards the open proximal end 3. The plunger 12 may include a piston 100 having a shaft 115 extending from a proximal thumb rest 110 to a distal stopper 20. In various embodiments, an attachment may be attached to the distal end 2 of the syringe 10 to facilitate delivery and/or movement of the fluid of the syringe body 1 to or from, for example, a blood vessel and/or the like of a human or an animal patient. Specific examples of attachments may include, for example, needles, catheters, tubes, and/or the like.

Figure 2:
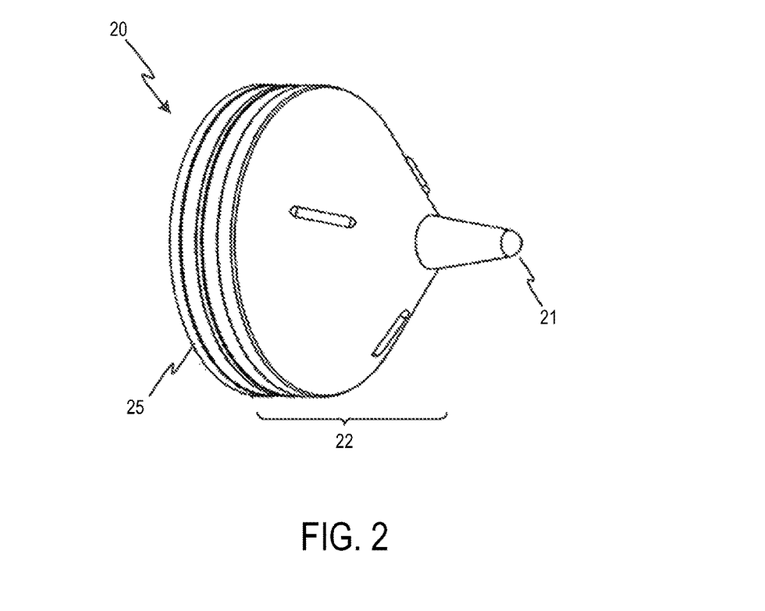
FIG. 2 depicts a stopper according to an embodiment.

The stopper 20 may generally have a circumference that is substantially equal to an inner circumference of the syringe body 1 and may be received by the open proximal end 3 of the syringe body. The stopper 20 may slidably move within the lumen 4 to facilitate movement of fluid within the syringe body 1. The type of fluid is not limited by this disclosure and may include any fluids including, for example, a pharmaceutical drug, a radiopharmaceutical, a contrast agent, a radioactive contrast agent, gene therapy fluid, and/or the like. In some embodiments, the stopper 20 may facilitate movement of the fluid towards and through the distal end 2 of the syringe 10. In other embodiments, the stopper 20 may facilitate movement of the fluid towards the proximal end 3 of the syringe 10. In particular embodiments, as shown in FIG. 2, the stopper 20 may have a cylindrical body 22 and a protrusion tip 21 sized and configured to substantially fill at least a portion of the conical shaped distal end 2 of the syringe body 1 (FIG. 1).

Referring back to FIG. 1, the piston 100 may provide a generally reciprocal movement of the stopper 20 through the syringe body 1. In some embodiments, movement of the stopper 20 and/or the piston 100 may allow for the fluid to be drawn into the lumen 4 of the syringe body 1 by placing the distal end 2 of the syringe body and/or an attachment thereto into the fluid and withdrawing the plunger 12. In some embodiments, movement of the stopper 20 and/or the piston 100 may allow for the fluid to be expelled from the lumen 4 of the syringe body 1 by advancing the piston into the syringe body. In some embodiments, the stopper 20 may be fixedly attached to a proximal end 105 of the piston 100. In other embodiments, the stopper 20 may be detachably connected to the proximal end 105 of the piston 100, allowing the piston to be removed and used with one or more different components discussed herein, such as stoppers and the like. For example, in the case of pre-filled syringes, various components may be reused to reduce the amount of disposable materials.

Figure 3:
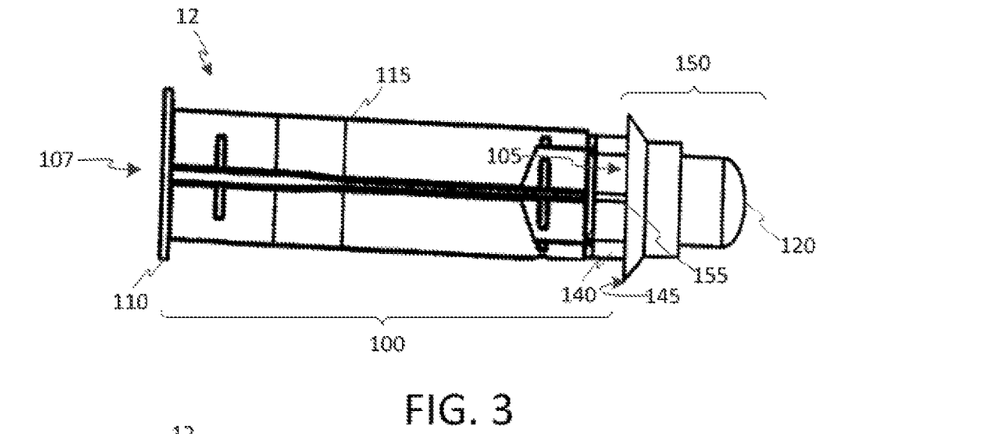
FIG. 3 depicts a piston according to an embodiment.
Figure 4A:
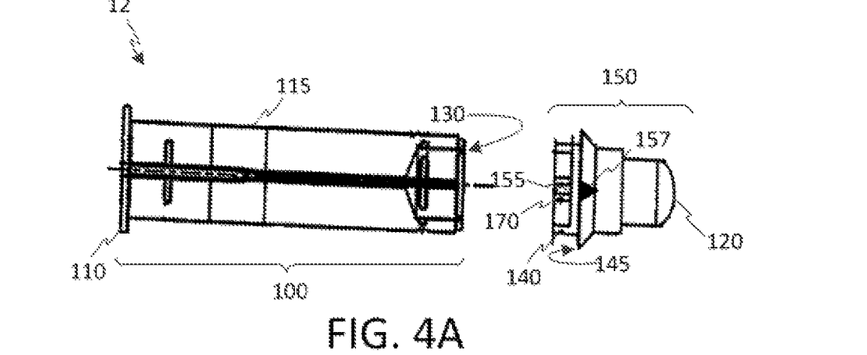
FIG. 4A depicts a piston having a separable coupler according to an embodiment.

As depicted in FIG. 3, the plunger 12 configured according to some embodiments may include, for example, a piston 100 having a proximal end 107 and a distal end 105. The proximal end 107 may include at least a thumb rest 110 that may be configured to be used by an operator to move the plunger 12 axially forward or backward within the syringe body 1 (FIG. 1). In some embodiments, a coupler 150 may be attached to the distal end 105 of a piston 100. Referring also to FIG. 4A, in some embodiments, a proximal end 135 of the coupler 150 may be detachably connected to a shaft 115 of the piston 100 using a fastening mechanism such as, for example, screws, snaps, rivets, and/or the like, as will be described in greater detail herein. In other embodiments, the coupler 150 may be fixedly attached to the shaft 115 using, for example, an adhesive. In still other embodiments, the coupler 150 may be a contiguous part of the piston 100 by, for example, injection molding the piston to include the coupler.

Figure 4B:
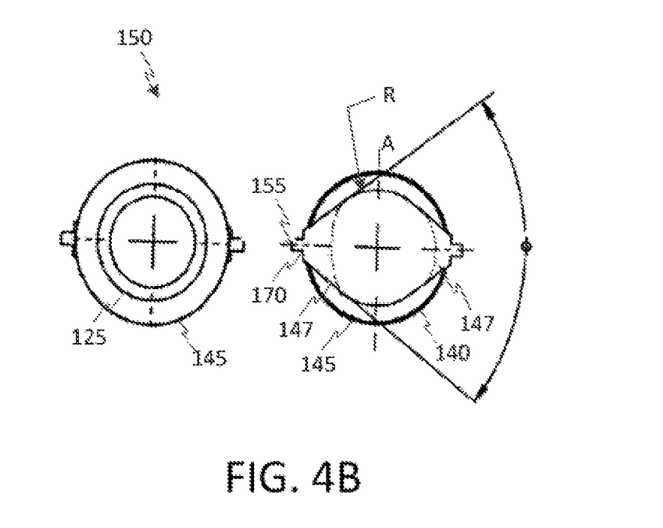
FIG. 4B depicts a cross-sectional top view and bottom view of a coupler according to an embodiment.
Figure 4C:
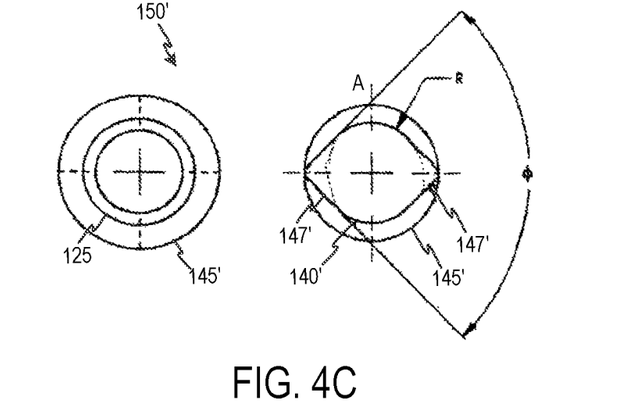
FIG. 4C depicts a cross-sectional top view and bottom view of an alternate coupler according to an embodiment.

In various embodiments, the coupler 150 may include a substantially circumferential groove 140 (or 140' in FIG. 4C) at a distal end 130 of the piston 100. In some embodiments, the groove 140 (or 140') may be continuous for the entire length of the coupler 150. In other embodiments, the circumferential groove 140 (or 140') may contain one or more gaps therein. In some embodiments, the groove 140 (or 140') may have at one or more extensions (element 147 in FIG. 4B or 147' in FIG. 4C)) extending radially from the groove. In particular embodiments, the groove 140 may include about 1 to about 8 extensions. In other particular embodiments, the groove 140 may include 2 extensions, 3 extensions, 4 extensions, 5 extensions, 6 extensions, or 8 extensions. The extensions 147 (or 147') may extend outwardly from the groove 140 (or 140') at least to an outer circumference of the piston 100. In some embodiments, the extensions 147 (or 147') may extend beyond the outer circumference of the piston 100. The extensions 147 (or 147') may have a substantially triangular shape, such as, for example, a substantially equilateral triangle, a substantially isosceles triangle, a right triangle, and the like. In some embodiments, the extensions 147 may include at least one or more notches 155 on one or more sides of the extensions on an outermost portion of each extension. The notches 155 may have any cross-sectional shape such as, for example, a square (as shown in FIG. 4B), a rectangle, a triangle, a circle, an ellipse, and/or the like. In various embodiments, the notches 155 may or may not be symmetrical. In some embodiments, the extensions 147 and the notches 155 may intersect in a flat 170 (FIG. 4A) such that the flat is substantially tangential to the outer surface of the extension.

Figure 4D:
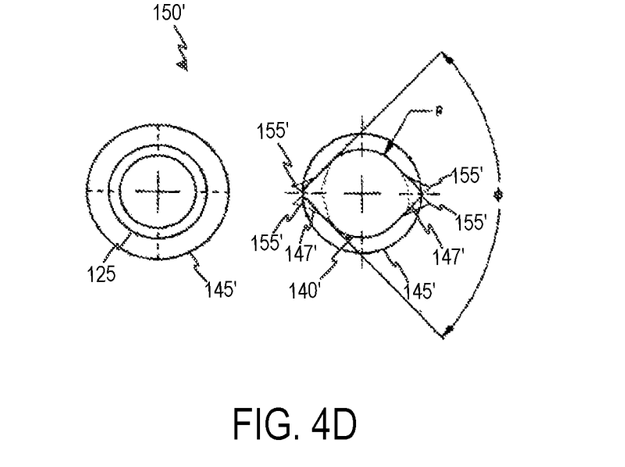
FIG. 4D depicts a separable coupler according to an embodiment.
Figure 5:
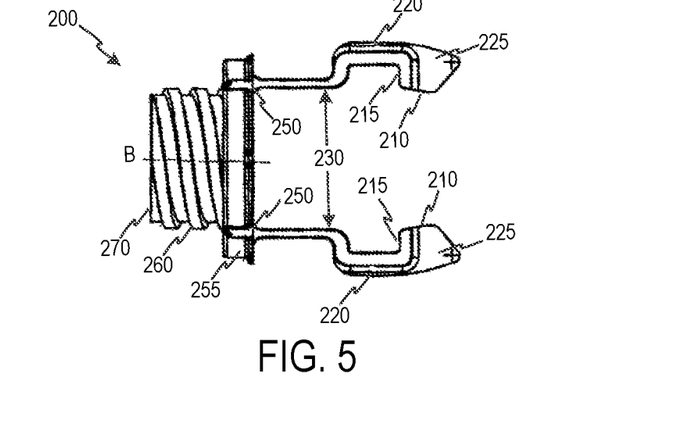
FIG. 5 depicts a side view of various parts of a clamping mechanism according to an embodiment.

In some embodiments, as illustrated in FIG. 4D, the notches 155' may extend from the surface of the extension 147'. The notches 155' may have, for example, a triangular cross-section having straight and/or curved sides, or any other shape (not shown). In some embodiments, the notches 155' may or may not be symmetrical. In various embodiments, an outermost edge of the notches 155' may extend beyond the outermost circumference of a tapered flange 145'. In some embodiments, the notches 155' may be angled to extend from the proximal end of the extensions 147' distally towards the tapered flange 145' forming a helical ridge. In some embodiments, the notches 155' may be tapered distally along the circumferential surface of the extensions 147'. Various embodiments may have one or more notches 155', such as, for example, two notches.

In some embodiments, the coupler 150 may include the tapered flange (145 in FIG. 3 or 145' in FIG. 4C) extending distally from the groove 140 (or 140'). In some embodiments, a maximum radius of the tapered flange 145 (or 145') may be equal to or shorter than the radius of the piston 100. In some embodiments, one or more deflectors 157 (FIG. 4A) may be disposed as one or more protuberances on the outer surface of the tapered flange 145 and may be axially distal to the notches 155. The shape of the deflectors is not limited by this disclosure, and may include any shape. Specific examples of deflector shapes may include conical shapes, hemispherical shapes, triangular shapes, and/or the like.

In various embodiments, the proximal end of the piston 100 may be detachably connected to one or more actuating mechanisms (not shown) such as, for example, a hydraulic assembly and/or an electric motor to aid the motion of the piston.

Referring to FIGS. 5 and 6A-6C, the distal portion of the piston 100 and/or the coupler 150 may be configured to engage the stopper 20 (FIG. 1) as described herein. In some embodiments, the stopper 20 (FIG. 1) may include at least a base 200 including one or more capture members 220 protruding rearwardly beyond the rear surface 255 of the base by an amount sufficient to capture and retain the tapered flange 145 of the coupler 150. The capture members 220 may be constructed of a flexible material such that the capture members flex outwardly when contacted by the tapered flange 145 and subsequently snap back to an original position after passing the tapered flange to engage the circumferential groove 140. While embodiments having two capture members 220 are shown and described here, embodiments having more than two capture members are also envisioned, depending on, among other things, the shape of the coupler and/or the number of extensions 147. The capture members 220 may include inwardly facing shoulders 215 that may be sized and designed to engage the circumferential groove 140 extending from each capture member on a proximal end of the capture member. In certain embodiments, the capture members 220 may further include extensions 225 extending proximally beyond the inwardly facing shoulders 215. In various embodiments, the base 200 may or may not be detachable from the stopper 20 (FIG. 1). In embodiments where the base 200 is detachable from the stopper 20, the base may have one or more helical threads 260 at its distal end 270 that may be configured to be screwed into an opening in the proximal end 25 of the stopper (FIG. 1).

Figure 6A:
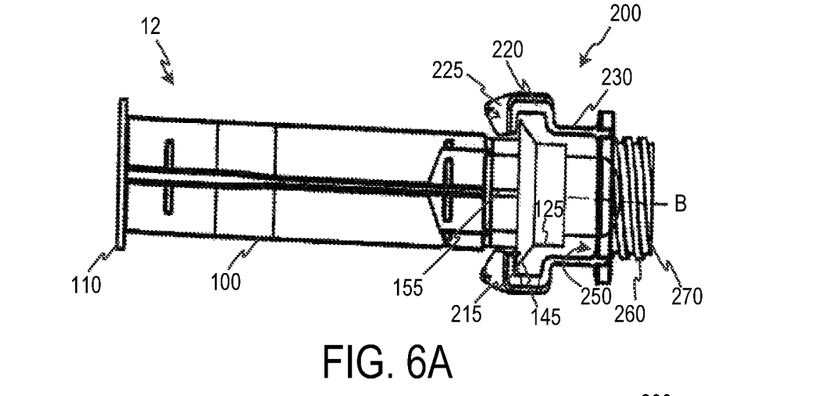
FIG. 6A depicts a clamping mechanism engaged with a piston according to an embodiment.
Figure 6B:
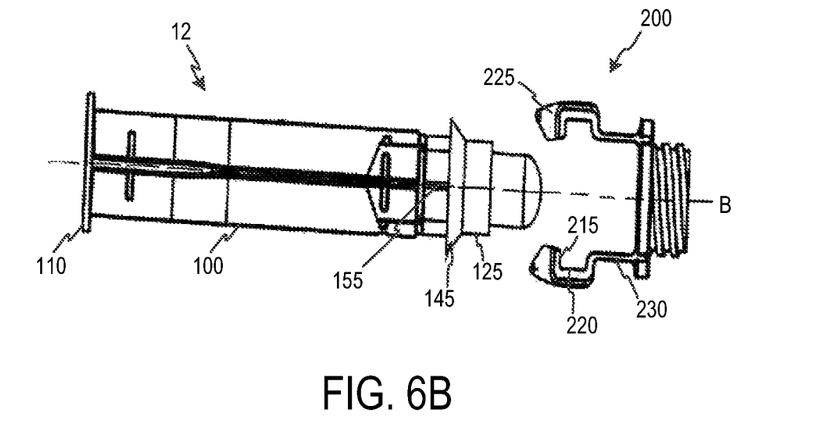
FIG. 6B depicts a piston disengaged from a clamping mechanism according to an embodiment.

As shown in FIG. 6A, in operation, the piston 100 may be positioned to contact the base 200 and engage the tapered flange 145. As the piston 100 is pushed against the base 200, the inwardly facing shoulders 215 may be forced outwardly until the tapered flange 145 passes beyond the shoulders of the capture members 220, as described in greater detail herein. This design may allow the piston 100 to stably engage with the stopper 20 (FIG. 1) at any axial position of the plunger 12 along the syringe axis without substantially dislocating the stopper from its position along the syringe axis. In some embodiments, the shoulders 215 may be aligned to engage the circumferential groove 140 when the stopper 20 (FIG. 1) is properly mounted in the syringe body 1. In some embodiments where the circumferential groove 140 contains one or more gaps as described herein, the gaps may allow the shoulders 215 to release up with a deflector to prevent the shoulders from being loaded in the gap. In embodiments having deflectors disposed on the tapered flange 145 as previously described herein, the deflectors may deflect the capture members 220 to prevent the capture members from lining up with the notches 155.

After retention of the coupler 150 (FIG. 3) by the capture members 220, the stopper 20 may resist disconnection from the piston 100 upon rearward movement of the piston. In some embodiments, the capture members 220 may be designed such that forces exerted on the capture members upon rearward movement of the piston 100 substantially prevent radially outward movement of the capture members. In some embodiments, shoulders 215 of the capture members 220 may be positioned such that the load experienced upon rearward movement of the piston 100 is at a position equal to or greater in radial distance relative to axis B than one or more anchors 250 where the capture members are attached to the base 200. Thus, a bending movement created by a rearward movement of the piston 100 may cause the capture members 220 to deflect radially inward and assist in preventing disconnection of the stopper 20 (FIG. 1) from the piston 100.

When the piston 100 is twisted about its axis B, the extensions 147 (or 147') may push the capture members 220 radially outward as the radial distance of the groove 140 surface increases allowing the piston to be disengaged from the stopper 20 upon rearward movement of the piston while it is twisted. In embodiments having notches 155 extending from the extensions 147, the notches may act as position indicators and/or twist-stops to stop the piston 100 from further twisting. In some embodiments, the flats 170 may provide positions at which the piston 100 may be disengaged from the stopper 20 (FIG. 1). This design may allow for detachment of the piston 100 from the stopper 20 with a twist of the piston that depends on the number of extensions 147 or the number of capture members 220. In particular embodiments, the twist of the piston 100 may be less than 180°, less than 120°, less than 90°, less than 72°, less than 60°, or less than 45°.

Figure 6C:
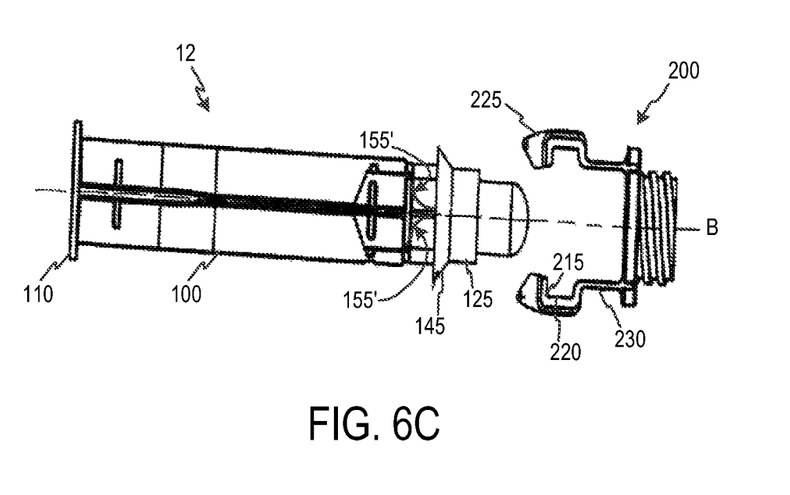
FIG. 6C depicts a piston disengaged from a clamping mechanism according to an embodiment

In embodiments such as those depicted in in FIGS. 4D and 6C, the piston 100 may be twisted about its axis B in such a manner that the notches 155' extending from the extensions 147' may push the beveled edges 210 (FIG. 5) of the capture members 220. In some embodiments, the beveled edges 210 (FIG. 5) may be pushed axially forward in a direction forward of the outer circumference of the tapered flange 145'. In some embodiments, the beveled edges 210 (FIG. 5) may be pushed such that the inwardly facing shoulders 215 of the base 200 are disengaged from the tapered flange 145'. This movement may disconnect the stopper 20 (FIG. 1) from the piston 100 when the stopper 20 is connected to the base 200. Additionally, in embodiments in which the notches 155' are formed as distally angled helical ridges on the extension 147' surface, twisting the piston 100 may result in pushing the beveled edges 210 radially outward by the extension surface and axially forward by the notches. As such, the inwardly facing shoulders 215 of the capture members 220 may clear the tapered flange 145' while the piston 100 is being twisted. In embodiments where a user attempts to attach the piston 100 in an orientation where the notches 155 extending from the extension 147' line up with the beveled edges 210, the one or more deflectors 157 (FIG. 4A) may push the beveled edges to either side of the deflector so that the beveled edges do not get stuck in the notches.

Figure 7A:
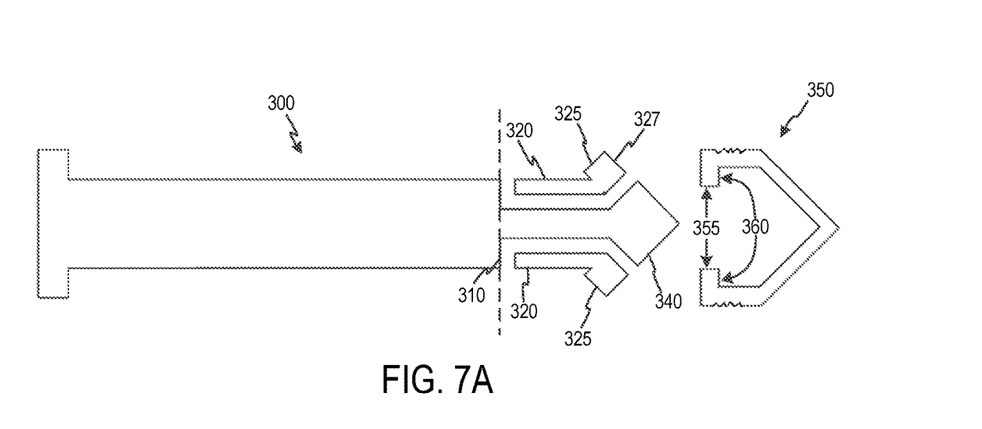
FIG. 7A depicts a piston disengaged from a clamping mechanism according to an embodiment.
Figure 7B:
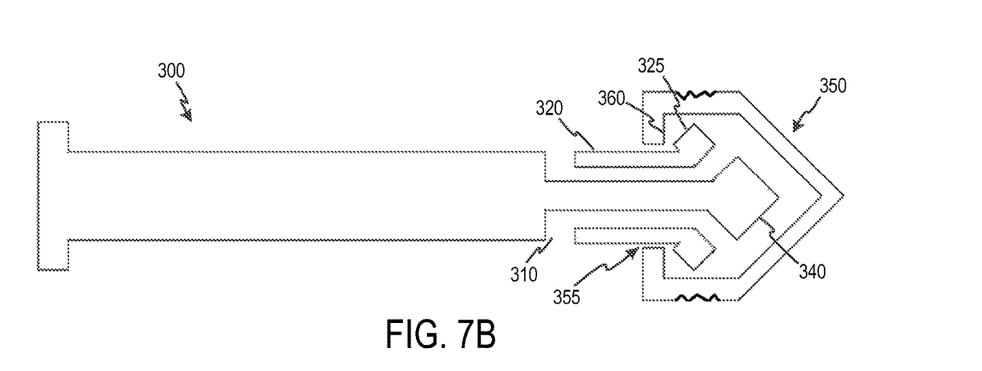
FIG. 7B depicts a piston engaged with a clamping mechanism according to an embodiment.

In various embodiments, as depicted in FIGS. 7A and 7B, one or more cantilevered capture members 320 may be disposed at the distal end of the piston 300 anchored from the distal wall 310 of the piston and disposed around a central extension 340 of the piston. In such embodiments, the capture members may have outwardly extending shoulders 325 and beveled surfaces 327 at the distal end of the capture members 320. In some embodiments, the piston 300 may have at least two capture members 320. In some embodiments, the piston 300 may have 2, 3, 4, 5, 6, or 8 capture members 320. In some embodiments, the piston 300 may have capture members 320 that may be symmetrically disposed around the central extension 340.

In various embodiments, the stopper 350 may have one or more retainer arms 360. In other embodiments, a base (not shown) having retainer arms 360 may be fabricated to fit into a stopper 20 for retrofitting one or more commercially available stoppers. As the piston 300 is moved forward through an opening 355 provided by the retainer arms 360 of in the stopper 350, the beveled edges 327 may tend to push the capture members 320 radially inward. Upon passing the retainer arms 360 of the stopper 350, the capture members 320 may snap back to engage the shoulders 325, thereby preventing the piston 300 from detaching from the stopper upon rearward movement of the piston. In various embodiments, the capture members 320 may be placed around the piston head 340 such that a rearward movement of the piston 300 pushes the capture members radially outward.

Figure 8:
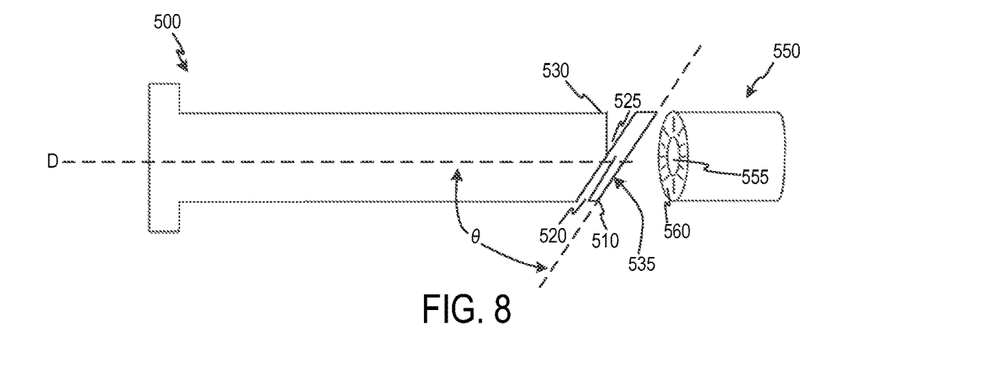
FIG. 8 depicts a piston having an angled end according to an embodiment.

As depicted in FIG. 8, some embodiments may include a piston 500 having a coupler that is an angled flange 510 contiguously connected to the piston 500 via a hinge 525 such that a distal surface 535 of the angled flange may form an angle θ, with the axis D of piston 500. In particular embodiments, the angle θ may be acute. In some embodiments, the hinge 525 may have an open position wherein the radially outermost portion of the distal surface 535 of the angled flange 510 extends no further than the outer wall 530 of the piston 500. In some embodiments, the hinge 525 of the angled flange 510 may have a closed position wherein the angled flange 510 tilts about the hinge at an increased angle θ.

In some embodiments, the plunger 12 may be operated by moving the piston 100 forward and twisting it. The angled flange 510 may engage with one or more threads 555 disposed on an inner wall of the stopper 550. Upon further forward movement, the angled flange 510 may tilt about the hinge 525, thereby placing the hinge in the closed position, and further engaging with the threads 555. This may prevent the piston 500 from detaching from the stopper 550 when moved in a rearward direction. Likewise, twisting in an opposite direction may disengage the angled flange 510 from the threads 555, thereby placing the hinge in the open position and allowing the piston 500 to be detached from the stopper 550. Such a design may allow for an easy engagement and/or detachment of the piston 500 from the stopper 550 in, for example, pre-filled syringes. Such a design may also allow for an easy engagement and/or detachment of any axial position of the stopper 550 without substantially dislocating the stopper from its axial position.

Figure 9:
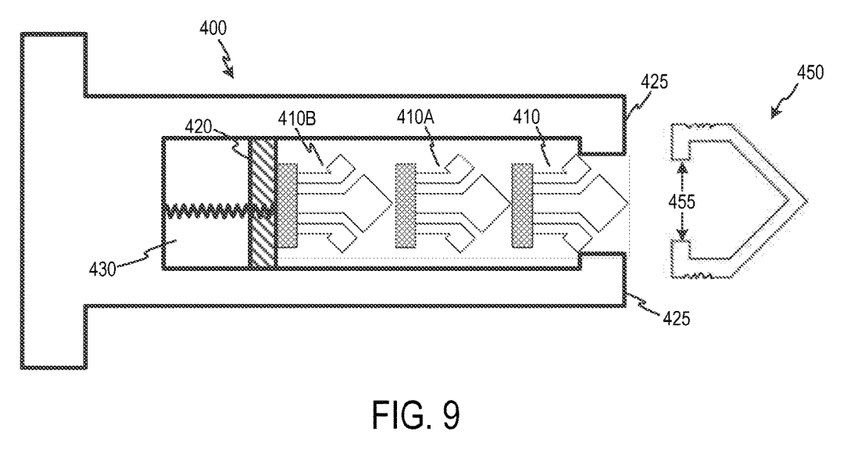
FIG. 9 depicts a piston having multiple, detachable couplers according to an embodiment.

As depicted in FIG. 9, some embodiments of the piston 400 may include a plurality of axially-stacked detachable couplers 410, 410A, 410B. In various embodiments, the plurality of couplers 410, 410A, 410B may be stacked on a spring loaded platform 420 in an axially disposed cavity 430 within the piston 400. Retainer arms 425 at the opening of the cavity 430 may prevent the end coupler 410 from receding back into the cavity 430. When using the piston 400, the end coupler 410 may be removed or detached from the piston after using the piston with a first syringe. Another coupler 410A (or 410B) may replace the removed end coupler 410 and become the new end coupler for using the piston 400 with a second (or a subsequent) syringe. In various embodiments, the end coupler 410 may be removed by any means of removal now known or later developed, such as, for example, twisting the piston 400, detaching the piston using the various quick-release mechanisms described herein, or breaking the end coupler off. In some embodiments, any number of couplers 410 may be loaded inside the cavity 430 for use, where the number of piston heads is only limited by the size of the cavity and/or the storage capability of the cavity. A specific number of piston heads may be, for example about 1 piston head to about 10 piston heads. In some embodiments, the detachable coupler 410 may reduce cross-contamination, such as, for instance, when a single piston 400 is used with multiple syringes, where one of the detachable couplers may be removed and disposed of after each use.

Figure 10:
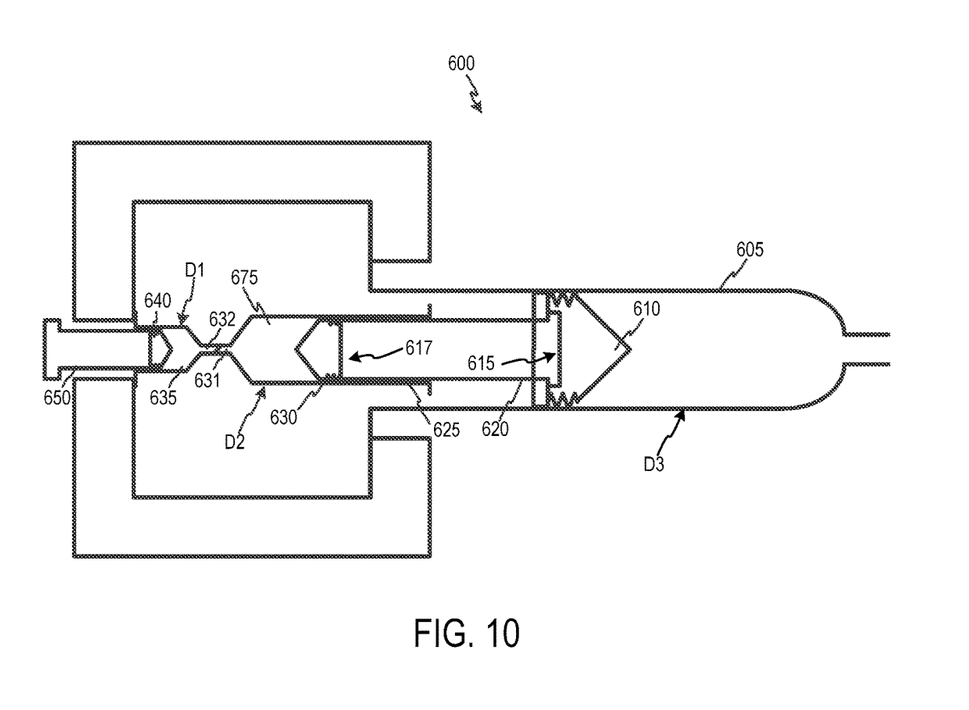
FIG. 10 depicts a piston having a hydraulic assist according to an embodiment.

In some embodiments, the piston may be part of a hydraulically activated or an electrically activated assembly. In some embodiments, for example, as depicted in FIG. 10, an internal piston 620 may have a hydraulic assist so as to reduce the force required by an operator using the syringe assembly 600 to deliver the contents of the syringe. A first syringe 605 portion of the syringe assembly 600 may have a diameter D3. The internal piston 620 may be connected to both the first syringe 605 and a second syringe 625 having a diameter D2. The diameter D2 of the second syringe 625 may generally be smaller than the diameter D3 of the first syringe 605. In some embodiments, the internal piston 620 may be connected to the first syringe 605 in such a manner that a proximal end 615 of the internal piston engages a first stopper 610 located in the first syringe. In some embodiments, the internal piston 620 may be connected to the second syringe 625 in such a manner that a distal end 617 of the piston engages a second stopper 630 located in the second syringe. A first tip 631 of the second syringe 625 may be connected to a second tip 632 of a third syringe 635. The third syringe 635 may have a diameter D1 that may be generally smaller than the diameter D2 of the second syringe 625.

In some embodiments, a lumen of the second syringe 625 and a lumen of the third syringe 635 may each be filled with an incompressible fluid 675. In particular embodiments, the incompressible fluid 675 may be sealed within the respective lumens of the second syringe 625 and the third syringe 635. An external piston 650 connected to the third syringe 635 may engage a plunger 640. When the external piston 650 is moved forward, the fluid 675 pushes the internal piston 620 which further pushes the first stopper 610. In some embodiments, because the fluid 675 is incompressible, the force placed upon the internal piston 620 is amplified by a factor of $(D2)^2/(D1)^2$ as the external piston 650 is moved forward. The diameters of various syringes 605, 625, 635 may be optimized by a skilled artisan depending on particular requirements for particular embodiments and/or usage thereof.

Figure 11:
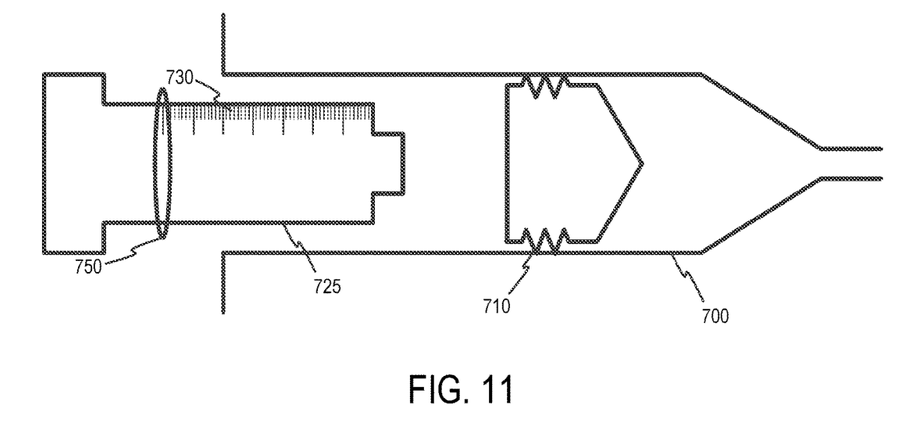
FIG. 11 depicts a piston having a volume measuring scale according to an embodiment.

In any of the various embodiments disclosed herein, it may be desirable to determine the total volume delivered using a plurality of syringes. Pistons of some embodiments may have a sliding scale or a marker system for indicating and/or measuring the volume of fluid disposed out of or collected into the syringe before the piston is detached. For example, as illustrated in FIG. 11, a piston 725 may have at least a measuring scale 730 configured to indicate a volume displaced by the plunger 710 after the piston 725 is engaged with the plunger and moved forward through the syringe 700. In some embodiments, the scale 730 may be detachably affixed to an O-ring 750 such that the O-ring detaches from the scale when piston 725 engages with the plunger 710 and attaches to the piston marking an initial volume. As the piston 725 is moved forward through the syringe 700, the scale 730 may slide along the O-ring 750, thus indicating the volume being delivered or removed. A user of the syringe 700 may determine the volume of a particular fluid delivered or removed by observing the scale 730 marked on the syringe. The O-ring 750 may indicate a total volume delivered at the end of delivery by the syringe 700, including the volume delivered from other syringes.

Although various embodiments have been described in detail for the purpose of illustration, it is to be understood that such detail is solely for that purpose and that the disclosure is not limited to the disclosed embodiments, but, on the contrary, is intended to cover modifications and equivalent arrangements. For example, it is to be understood that this disclosure contemplates that, to the extent possible, one or more features of any embodiment can be combined with one or more features of any other embodiment.

What is claimed is:

1. A stopper within a body of a syringe to facilitate movement of fluid within the syringe, the stopper comprising:
   a base detachably affixed into an opening in a proximal end of the stopper; and
   two capture members, the two capture members arranged opposite one another on a proximal surface of the base and extending rearwardly from the proximal surface of the base, each of the two capture members comprising a beveled edge;
   wherein the beveled edge is configured to interact with a piston of a fluid injection apparatus and wherein the two capture members are radially outwardly deflected upon rotation of the stopper relative to the piston to facilitate removal of the stopper from the piston, and wherein the stopper is configured for slidable movement within the body of the syringe and forms a fluid tight seal with an inner wall of the body of the syringe.

2. The stopper according to claim 1, wherein each of the two capture members comprise an inwardly facing shoulder.

3. The stopper according to claim 2, wherein the two capture members extend rearwardly from the base by an amount sufficient to releasably capture and retain a tapered flange on the piston.

4. The stopper according to claim 3, wherein the inwardly facing shoulder of each of the two capture members are configured to engage a circumferential groove proximal to the tapered flange on the piston.

5. The stopper according to claim 4, wherein the two capture members are formed from a flexible material such that each of the capture members flexes radially outward when contacted by a taper of the tapered flange and subsequently snap back to an original position after passing the tapered flange to engage the circumferential groove.

6. The stopper according to claim 4, wherein the stopper is configured to resist disconnection from the piston upon rearward movement of the piston.

7. The stopper according to claim 4, wherein upon rearward movement of the piston radially outward movement of the two capture members is prevented.

8. The stopper according to claim 7, wherein a bending movement of each of the two capture members created by a rearward movement of the piston causes the two capture members to deflect radially inward.

9. The stopper according to claim 2, wherein the two capture members further comprise one or more extensions extending proximally from the inwardly facing shoulder.

10. The stopper according to claim 1, wherein the base comprises one or more helical threads to detachably affix the base to the opening in the proximal end of the stopper.

11. The stopper according to claim 3, wherein upon rotation of the stopper relative to the piston, the beveled edge is configured to be pushed radially outward such that the inwardly facing shoulders of the two capture members are disengaged from the tapered flange.

12. The stopper according to claim 1, wherein the stopper comprises a cylindrical body and is configured to substantially fill at least a portion of a conical shaped distal end of the syringe.

13. A plunger apparatus comprising:
   a stopper removably configured to slidably move within a hollow lumen of a syringe to facilitate movement of fluid within the syringe, the stopper comprising:
      a base detachably affixed into an opening in a proximal end of the stopper; and
      two capture members arranged opposite one another on a proximal surface of the base and extending rearwardly from the proximal surface of the base, the two capture members each comprising a beveled edge and an inwardly facing shoulder,
      wherein the beveled edge is configured to interact with a piston of a fluid injection apparatus and wherein the two capture members are radially outwardly deflected upon rotation of the stopper relative to the piston to facilitate removal of the stopper from the piston.

14. The plunger apparatus of claim 13, further comprising a coupler for connection to a distal portion of the piston, wherein the coupler comprises a substantially circumferential groove and is configured to facilitate removable attachment of the stopper to the piston and wherein the inwardly facing shoulders of the two capture members are configured for releasably engaging the circumferential groove.

15. The plunger apparatus of claim 14, wherein the coupler is fixedly attached to the distal portion of the piston.

16. The plunger apparatus of claim 14, wherein the two capture members are configured to move radially outward as a radial distance of the circumferential groove increases upon rotation of the stopper relative to the piston, allowing the piston to be detached from the stopper.

17. The plunger apparatus of claim 14, wherein the coupler comprises a tapered flange extending distally from the circumferential groove, wherein the tapered flange is configured to removably secure the coupler to the stopper by locking with the two capture members of the stopper.

18. The plunger apparatus of claim 13, wherein each of the two capture members is constructed of a flexible material such that each of the two capture members flex outwardly when contacted by a tapered flange and subsequently snap back to an original position after passing the tapered flange to engage a circumferential groove on the piston.

19. The plunger apparatus of claim 13, wherein the two capture members protrude rearwardly beyond a rear surface of the base by an amount sufficient to capture and retain a tapered flange on the piston to resist disconnection of the stopper from the piston.

\* \* \* \* \*

UNITED STATES PATENT AND TRADEMARK OFFICE
CERTIFICATE OF CORRECTION

PATENT NO. : 10,286,152 B2
APPLICATION NO. : 15/687641
DATED : May 14, 2019
INVENTOR(S) : Cowan et al.

Page 1 of 1

It is certified that error appears in the above-identified patent and that said Letters Patent is hereby corrected as shown below:

In the Specification
In Column 4, Line 55, delete "have at" and insert -- have --, therefor.

Signed and Sealed this
Sixth Day of August, 2019

Andrei Iancu
*Director of the United States Patent and Trademark Office*